(12) United States Patent
Shibata et al.

(10) Patent No.: US 11,097,251 B2
(45) Date of Patent: Aug. 24, 2021

(54) METHOD FOR PRODUCING POROUS CELLULOSE MEDIUM

(71) Applicant: DAICEL CORPORATION, Osaka (JP)

(72) Inventors: Toru Shibata, Himeji (JP); Yuki Hirabayashi, Himeji (JP)

(73) Assignee: DAICEL CORPORATION, Osaka (JP)

( * ) Notice: Subject to any disclaimer, the term of this patent is extended or adjusted under 35 U.S.C. 154(b) by 102 days.

(21) Appl. No.: 16/097,924

(22) PCT Filed: May 12, 2017

(86) PCT No.: PCT/JP2017/017983
§ 371 (c)(1),
(2) Date: Oct. 31, 2018

(87) PCT Pub. No.: WO2017/195884
PCT Pub. Date: Nov. 16, 2017

(65) Prior Publication Data
US 2019/0126238 A1     May 2, 2019

(30) Foreign Application Priority Data

May 13, 2016    (JP) .............. JP2016-096872

(51) Int. Cl.
*B01J 20/24*     (2006.01)
*B01D 15/34*     (2006.01)
(Continued)

(52) U.S. Cl.
CPC .............. *B01J 20/24* (2013.01); *B01D 15/34* (2013.01); *B01D 15/3809* (2013.01);
(Continued)

(58) Field of Classification Search
CPC ..... B01J 20/24; C08J 9/28; C08L 1/12; C08F 251/02
See application file for complete search history.

(56) References Cited

U.S. PATENT DOCUMENTS 2,459,927 A *   1/1949   Andersen .................. C08L 1/12
                                               264/343
2,986,558 A *   5/1961   Ultee ..................... C08F 236/16
                                               536/56
(Continued)

FOREIGN PATENT DOCUMENTS

EP         0 560 891 A1     9/1993
JP         57-159801 A     10/1982
(Continued)

OTHER PUBLICATIONS

Bai et al., "Preparation and characterization of crosslinked porous cellulose beads", Carbohydrate Polymers, 2006, vol. 64, pp. 402-407.
(Continued)

*Primary Examiner* — Ryan B Huang
(74) *Attorney, Agent, or Firm* — Birch, Stewart, Kolasch & Birch, LLP.

(57) ABSTRACT

Provided is a novel method by which a porous cellulose medium is able to be suitably produced from cellulose acetate. A method for producing a porous cellulose medium, which comprises: a step for preparing a cellulose acetate solution wherein cellulose acetate is dissolved in a solvent; and a step for obtaining a mixed solution by mixing the cellulose acetate solution, a deacetylating agent and a catalyst with each other.

13 Claims, 3 Drawing Sheets

(51) Int. Cl.
    *C08J 9/28*     (2006.01)
    *B01J 20/30*     (2006.01)
    *B01D 15/38*     (2006.01)
    *B01J 20/28*     (2006.01)
    *C07K 1/22*     (2006.01)
    *C07K 16/06*     (2006.01)

(52) U.S. Cl.
    CPC ......... *B01J 20/28042* (2013.01); *B01J 20/30* (2013.01); *B01J 20/3085* (2013.01); *C07K 1/22* (2013.01); *C07K 16/065* (2013.01); *C08J 9/28* (2013.01); *C08J 2207/10* (2013.01); *C08J 2301/12* (2013.01)

(56) References Cited

U.S. PATENT DOCUMENTS

| | | | |
|---|---|---|---|
| 4,118,336 A * | 10/1978 | Morishita | B01J 13/06 424/494 |
| 4,638,057 A * | 1/1987 | Takahashi | A01N 25/18 239/34 |
| 5,026,841 A | 6/1991 | Francotte et al. | |
| 5,240,665 A * | 8/1993 | Seo | C08K 3/16 264/169 |
| 5,371,211 A | 12/1994 | Faber | |
| 5,658,561 A * | 8/1997 | Nakabayashi | A61L 33/0088 424/424 |
| 2003/0012941 A1 | 1/2003 | Fujita et al. | |
| 2003/0186041 A1 | 10/2003 | Fujita et al. | |
| 2008/0070027 A1 | 3/2008 | Fujita et al. | |
| 2016/0200835 A1* | 7/2016 | Kurabayashi | B01J 39/05 536/71 |
| 2017/0210871 A1* | 7/2017 | Shibata | B01J 20/3078 |
| 2018/0043333 A1 | 2/2018 | Shibata et al. | |

FOREIGN PATENT DOCUMENTS

| | | | | |
|---|---|---|---|---|
| JP | 60126371 A | * | 7/1985 | |
| JP | 62-277401 A | | 12/1987 | |
| JP | 63-95237 A | | 4/1988 | |
| JP | 2-53801 A | | 2/1990 | |
| JP | 5-255066 A | | 10/1993 | |
| JP | 11-158202 A | | 6/1999 | |
| WO | WO 2016/013568 A1 | | 1/2016 | |
| WO | WO-2016013568 A1 | * | 1/2016 | ............ C07K 16/00 |
| WO | WO 2016/159334 A1 | | 10/2016 | |

OTHER PUBLICATIONS

Chen et al., "Physical Characteristics of Porous Cellulose Beads as Supporting Material for Immobilized Enzymes", Biotechnology and Bioengineering, 1976, vol. 18, pp. 1507-1516.

International Search Report (PCT/ISA/210) issued in PCT/JP2017/017983, dated Aug. 8, 2017.

Reuvers et al., "Demixing and Gelation Behavior of Ternary Cellulose Acetate Solutions", Journal of Polymer Science: Part B Polymer Physics, 1986, vol. 24, pp. 793-804.

Yukimori et al., "Cellulose-kei Kobunshimaku no Nisankatanso Toka Bunri Kyodo", SCEJ 42nd Autumn Meeting (Kyoto,2010), 2010, 2. Experiment, 3.Results and Study, 1 page.

Enomoto-Rogers et al., "Water-soluble low-molecular-weight cellulose chains radically oriented on gold nanoparticles," Cellulose (2011), vol. 18, pp. 929-936.

Extended European Search Report dated Nov. 12, 2019, in European Patent Application No. 17796242.0.

St. John Manley, R. "Hydrolysis of Cellulose Tiracetate Crystals," Journal of Polymer Science: Part A (1963), vol. 1, pp. 1893-1899.

* cited by examiner

METHOD FOR PRODUCING POROUS CELLULOSE MEDIUM

TECHNICAL FIELD

The present invention relates to a method for producing a porous cellulose medium.

BACKGROUND ART

Polysaccharides typified by cellulose, and derivatives thereof are used for various purposes. For example, such a microporous material can itself serve as an adsorbent, and by subjecting a surface thereof to some chemical modification, an absorption or separation function can be imparted.

In recent years, separation and purification of biopolymers such as proteins has become one of important technical challenges due to popularization of use of enzymes, development of biopharmaceuticals, and the like. Chromatography is important means for solving the challenge. In chromatography, a separating agent is used in which some atomic group (often referred to as a selector) that interacts with a target or an impurity to be removed is bonded to a solid called a matrix.

Absence of nonspecific adsorption of proteins is very important property as a material for separating biopolymers, and therefore a polysaccharide is heavily used as a matrix. In addition, a polysaccharide has many hydroxyl groups in the molecule, and is therefore capable of easily bonding a selector through an ether bond or an ester bond with the hydroxyl groups as a scaffold, and this is also a major factor of heavily using a polysaccharide.

In addition, for separating and purifying a biopolymer, a method is generally used in which a selector having some affinity with target molecules is bonded to a matrix to adsorb the target molecules, and the adsorbed target molecules are released and recovered by some method. Capability of bonding a large amount of a selector is required for obtaining a large amount of target molecules. Further, for ensuring that the selector and a biopolymer having a large molecular weight efficiently interact with each other, the matrix is required to have a porous structure which allows target molecules to freely enter and leave. In other words, it is necessary to exhibit an exclusion limit larger than the total size of molecules to be purified and a ligand when the matrix is packed in a column to perform size-exclusion chromatography.

Such a matrix is often packed as particles in a tube called a column when used. On the other hand, a new form which has attracted attention in recent years is an integrated porous material called a monolith. The porous material is placed in a capillary called a capillary or a container such as a column, and is used for the same purpose as described above. A monolith having a relatively small thickness and a large area can also be used as a filtration membrane.

Ease of use of such a matrix is ascribable to high physical strength in addition to selectivity for separation targets. That is, a matrix having a low elastic modulus suffers from compressive deformation and breakage when a liquid or a gas flows in chromatography or filtration. As a result, the flow of a liquid in a chromatography column becomes nonuniform, and further the column is clogged, so that the separation efficiency of the column is markedly reduced. High physical strength is important property, and in this respect, cellulose is an excellent material among polysaccharides.

In addition, cellulose has an advantage that a variety of atomic groups can be bonded through chemical reaction because alcoholic hydroxyl groups are present on the surface as a general feature of polysaccharides; a large amount of a material having a high purity can be relatively inexpensively obtained; and so on.

For the reasons described above, a porous cellulose medium which is mainly intended to separate and purify a biopolymer has been developed. As a method for producing the porous cellulose medium, a method is known in which cellulose is dissolved by some method, and then regenerated. On the other hand, there are several methods using an organic acid ester as a starting material. These methods make use of an advantage that while it is difficult to directly dissolve cellulose itself because a special solvent is required, and the solution has a very high viscosity, an organic acid ester can be dissolved in many solvents; organic acid esters of cellulose with various bonding ratios with various organic acids and various polymerization degrees are supplied under stable quality on an industrial scale; industrially supplied with organic acid esters of ester bonds can be easily decomposed to regenerate cellulose; and so on.

As a method for producing a porous cellulose medium, for example, Patent Document 1 suggests that a solution of a cellulose organic acid ester in an organic solvent such as halogenated hydrocarbon is dispersed in an aqueous medium to form fine droplets of an ester solution, and a hydrolysis accelerating agent such as an ammonium salt is added thereto to hydrolyze the ester, thereby forming cellulose fine particles.

In addition, Patent Document 2 discloses a method in which a cellulose fatty acid ester and a gelling agent for the cellulose fatty acid ester are dissolved in an organic solvent to obtain a solution, the solution is added to an aqueous medium with stirring to form droplets, a coagulation accelerating agent is added to form the cellulose fatty acid ester into gel particles, and the gelling agent, the coagulation accelerating agent, and the solvent are removed from the generated particles to produce porous spherical particles.

Patent Document 3 discloses a method in which cellulose is dissolved in a mixed liquid of paraformaldehyde and dimethylsulfoxide, the solution is dispersed in a dispersion medium, and a silicon compound is then added as a coagulant to coagulate dispersed droplets of cellulose into a gel, thereby preparing a particulate cellulose gel.

Non-Patent Document 1 discloses a method in which cellulose acetate is dissolved in a water-soluble organic solvent (a mixed solvent of acetone and DMSO), and the solution is dispersed in water, so that the solution containing cellulose acetate comes into contact with water to be solidified, thereby forming porous particles.

Non-Patent Document 2 discloses that cellulose diacetate is dissolved in DMSO, anhydrous sodium sulfate is then added, and the mixture is stirred, and put in an acid coagulation bath (hydrochloric acid) to obtain cellulose particles (beads). The document also discloses means for removing sodium sulfate by immersing collected beads in a large amount of hot water in order to enhance the porosity of the beads. Non-Patent Document 3 reports that a homogeneous composition containing a solvent including water and cellulose acetate undergoes a phase transition (liquid form-gel form) to turn into a gel at a certain temperature or a lower temperature.

PRIOR ART DOCUMENTS

Patent Documents

Patent Document 1: Japanese Patent Laid-open Publication No. 62-277401

Patent Document 2: Japanese Patent Laid-open Publication No. 63-95237

Patent Document 3: Japanese Patent Laid-open Publication No. 57-159801

Non-Patent Documents

Non-Patent Document 1: Chen, L. F.; Tsao, G. T. Biotechnol. Bioeng. 1976, 18, 1507

Non-Patent Document 2: Bai, Y.-X.; Li, Y.-F. Carbohydr. Polym. 2006, 64, 402

Non-Patent Document 3: A. J. Reuvers et al., J. Polym. Sci., 1986, 24, 793

DISCLOSURE OF THE INVENTION

Problems to be Solved by the Invention

For example, in the methods of Patent Documents 1 and 2, a solvent containing a halogenated hydrocarbon is used, and removal of the solvent is performed by vaporization in preparation of particles, and therefore the methods require large energy, and an apparatus for recovering the vaporized solvent. In addition, in a method using a coagulation accelerating agent or a coagulant as described in Patent Documents 2 and 3, a dense cellulose fatty acid ester layer may be formed at a portion that is in contact with the coagulation accelerating agent or the like in the formed droplets, leading to a distorted particle shape. Accordingly, as described in Patent Documents 2 and 3, unevenness may occur in reaction when gelation is performed after droplets are formed.

In addition, Non-Patent Document 1 suggests that beads are crosslinked by subjecting the formed beads to crosslinking reaction with formaldehyde and hydrochloric acid. In addition, Non-Patent Document 2 suggests that a pore forming agent is used for prowling pores in particles. However, in both of Non-Patent Document 1 and Non-Patent Document 2, formation of particles include a step of treating the surfaces thereof, and for obtaining porous cellulose particles, it is necessary to remove a substance used for surface treatment.

Thus, various methods are known for producing a porous cellulose medium, and a novel method capable of suitably producing a porous cellulose medium from cellulose acetate is further required.

Under these circumstances, a main object of the present invention is to provide a novel method capable of suitably producing a porous cellulose medium from cellulose acetate.

Means for Solving the Problem

The present inventors have extensively conducted studies for achieving the above-mentioned object. Resultantly, the present inventors have found that a porous cellulose medium can be suitably produced by a method for producing a porous cellulose medium, the method including the steps of preparing a cellulose acetate solution with cellulose acetate dissolved in a solvent; and mixing the cellulose acetate solution, a deacetylating agent and a catalyst. More specifically, in the present invention, the rate of deacetylation of cellulose acetate by the deacetylating agent can be adjusted by adjusting the amount and type of the catalyst in a mixed solution containing cellulose acetate. The present inventors have found that accordingly, for example, when the porous cellulose medium is produced in the form of porous cellulose particles, adjustment of the amount and type of the catalyst enables the mixed solution to turn into a gel at a desired rate in a state in which the mixed solution is dispersed, so that porous cellulose particles formed from a porous cellulose medium are suitably produced. In addition, the present inventors have found that for example, when the porous cellulose medium is produced in the form of a porous cellulose monolith, adjustment of the amount and type of the catalyst enables the mixed solution to turn into a gel at a rate which allows a porous structure to be formed in the monolith. The present invention has been completed by further conducting studies based on the above-mentioned findings.

Item 1. A method for producing a porous cellulose medium, the method including the steps of:

preparing a cellulose acetate solution with cellulose acetate dissolved in a solvent; and mixing the cellulose acetate solution, a deacetylating agent, and a catalyst to obtain a mixed solution.

Item 2. The method for producing a porous cellulose medium according to item 1, wherein the catalyst is at least one selected from the group consisting of an alkoxide, an amine compound, a weak-basic inorganic compound, and a N-hydroxyamine derivative.

Item 3. The method for producing a porous cellulose medium according to item 2, wherein the amine compound is a tertiary amine, and the weak-basic inorganic compound is a carbonate.

Item 4. The method for producing a porous cellulose medium according to any one of items 1 to 3, wherein a porous cellulose monolith formed from a porous cellulose medium is obtained by allowing deacetylation reaction of the cellulose acetate to proceed in a state in which the mixed solution is left standing in a molding container.

Item 5. The method for producing a porous cellulose medium according to any one of items 1 to 4, wherein porous cellulose particles formed from a porous cellulose medium are obtained by mixing the mixed solution with a dispersion medium immiscible with the mixed solution, and allowing deacetylation reaction of the cellulose acetate to proceed in a state in which the mixed solution is dispersed.

Item 6. The method for producing a porous cellulose medium according to item 5, wherein the dispersion medium is liquid paraffin.

Item 7. A method for producing an adsorbent, the method including the step of immobilizing an affinity ligand on the porous cellulose medium obtained by the method according to any one of items 1 to 6.

Item 8. The method for producing an adsorbent according to item 7, wherein the affinity ligand is at least one selected from the group consisting of protein A, protein G, protein L, and functional variants thereof.

Item 9. A method for purifying a target substance, the method including:

a first step of bonding the target substance to an affinity ligand by bringing an adsorbent, which is obtained by bonding the affinity ligand to the porous cellulose medium obtained by the production method according to any one of Items 1 to 6, into contact with a mixture containing the target substance; and a second step of separating the target substance bonded to the affinity ligand of the adsorbent.

Advantages of the Invention

According to the present invention, it is possible to provide a novel method capable of suitably producing a porous cellulose medium from cellulose acetate.

EMBODIMENTS OF THE INVENTION

Figure 1:
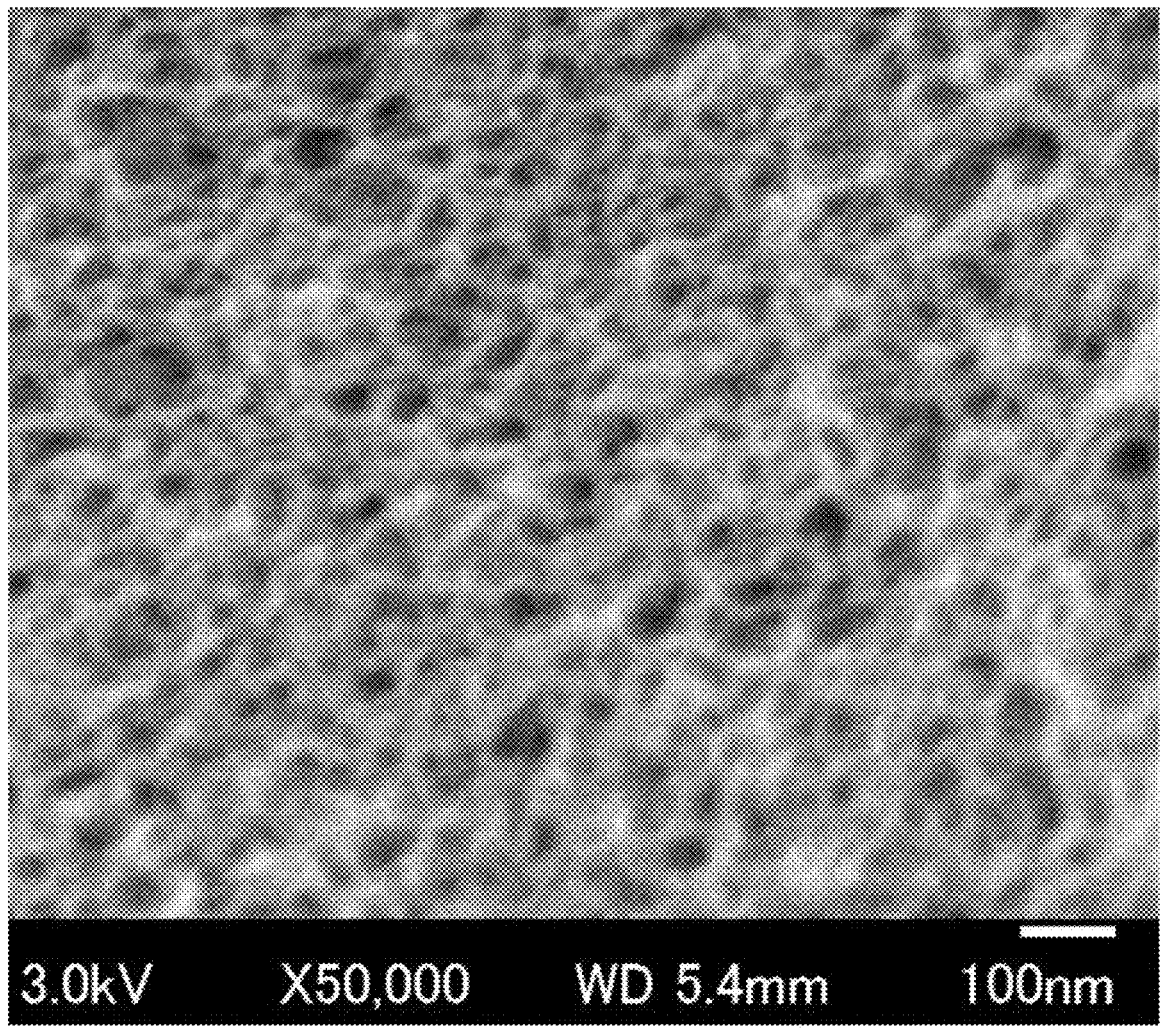
FIG. 1 is an image of an election micrograph of a broken surface of a solid obtained in Example 1.

A method for producing a porous cellulose medium according to the present invention includes the steps of: preparing a cellulose acetate solution with cellulose acetate dissolved in a solvent; and mixing the cellulose acetate solution, a deacetylating agent, and a catalyst to obtain a mixed solution. The method for producing a porous cellulose medium according to the present invention has a configuration as described above, and is thus capable of suitably producing a porous cellulose medium from cellulose acetate. Hereinafter, the method for producing a porous cellulose medium according to the present invention will be described in detail.

In the method for producing a porous cellulose medium according to the present invention, a cellulose acetate solution with cellulose acetate dissolved in a solvent, a deacetylating agent, and a catalyst are mixed, and a porous cellulose medium is produced by utilizing a phenomenon in which in the mixed solution, deacetylation of cellulose acetate proceeds, leading to occurrence of a liquid-gel phase transition.

In the present invention, the liquid-gel phase transition by deacetylation is a phenomenon in which the liquid mixed solution having fluidity loses fluidity as deacetylation reaction proceeds. For example, a phenomenon in which the viscosity increases as the temperature decreases is found in many solutions, and in gelation from a liquid, fluidity is substantially completely eliminated, and in many cases, the resulting gel becomes clouded. In the present invention, a cellulose acetate solution with cellulose acetate dissolved in a solvent, a deacetylating agent, and a catalyst are mixed, so that deacetylation reaction of cellulose acetate proceeds to cause gelation.

In the production method of the present invention, first a cellulose acetate solution with cellulose acetate dissolved in a solvent is prepared. The cellulose acetate is not limited as long as it undergoes the phase transition by deacetylation. Typical physical properties of cellulose acetate may include the polymerization degree and the substitution degree. By appropriately adjusting the polymerization degree and the substitution degree of cellulose acetate, conditions under which deacetylation causing a liquid-gel phase transition occur can be adjusted.

The polymerization degree is preferably 50 or more in terms of a weight average for increasing the mechanical strength of the resulting porous cellulose medium to prevent elution into a solvent or the like at the time of use. On the other hand, for the upper limit of the polymerization degree, any available cellulose acetate can be used.

The substitution degree has a strong influence on the solubility of cellulose acetate. The substitution degree is a numerical value indicating how many hydroxyl groups are substituted among the three hydroxyl groups of one glucose residue of cellulose. In the case of the acetate, the substitution degree may be expressed as acetic acid content or acetyl group content, and these contents can be converted into each other. Generally, the acetate having a substitution degree of about 2.8 to 2.9 is distributed as a triacetate, and acetate having a substitution degree of about 2.5 is distributed as a diacetate. In the present invention, the substitution degree is not limited as long as the acetate causes the phase transition.

Cellulose acetate that is generally distributed includes so-called cellulose diacetate which is commonly used as a fiber material or the like (in particular, a typical product has an acetyl substitution degree of 2.5, or an acetic acid content of about 55% (acetylation degree)); and triacetate which is used as a film material for photography or liquid crystal display (having an acetyl substitution degree of 2.8 to 2.9, or an acetic acid content of 60% (acetylation degree)). Cellulose acetate having a substitution degree of about 1 (which may be referred to as monoacetate, but the name is not established as a common name because such an acetate is not generally distributed) may be dissolved in water, and there are a wide range of options of polar solvent systems. Such a grade of cellulose acetate which is not generally distributed can be obtained by, for example, performing solvolysis by adding a calculated amount of a base to a solution of cellulose acetate having a higher substitution degree, or hydrolyzing a water-containing acetic acid solution of the cellulose acetate with an acid catalyst such as sulfuric acid, and stopping the reaction at an appropriate timing (neutralizing sulfuric acid). For example, such cellulose acetate can be obtained by reacting 1.5 equivalents of a base per glucose unit with a diacetate (cellulose diacetate) as a starting material. As the base, hydrazine and hydroxylamine, which are neutral molecules, and therefore easily miscible with many organic solvents and which rapidly react, are conveniently used, but in short, a hydroxide, e.g. quaternary ammonium hydroxide or the like can be used as long as it is a base miscible with a raw material solution.

A triacetate, a diacetate, and a monoacetate are not clearly discriminated from one another in terms of an acetylation degree, but in the present invention, for the sake of convenience, an acetate having an acetylation degree of 2.7 or more is defined as a triacetate, an acetate having an acetylation degree of 1.5 or more and less than 2.7 is defined as a diacetate, and an acetate having an acetylation degree of 0.5 or more and less than 1.5 is defined as a monoacetate.

The solvent for dissolving cellulose acetate is not particularly limited as long as it can dissolve cellulose acetate, but since this reaction uses a base catalyst, an acidic solvent which quenches the reaction, such as acetic acid, is not preferable, and a polar solvent having a high capability of dissolving a deacetylating agent and a catalyst is preferable. Examples of the solvent include polar solvents such as tetrahydrofuran (THF), dimethyl ether (DME), ethylene glycol monomethyl ether, ethylene glycol monoethyl ether, diethylene glycol monomethyl ether, diethylene glycol monoethyl ether, trifluoroethanol, acetamide, and formamide; and aprotic polar solvents such as dimethylsulfoxide (DMSO), sulfolane, dimethylsulfone, N-methylpyrrolidone, N,N-dimethylacetamide, N,N-dimethylformamide, N,N'-dimethylimidazolidinone, hexamethylphosphorotriamide, and tetramethylurea. In addition, when particles are prepared by dispersion in a dispersion medium as described later, it is necessary that the solvent and the dispersion medium should not be mixed. Examples of the particularly preferable solvent which satisfies these conditions, and are not miscible with liquid paraffin that is, for example, an inexpensive dispersion medium, and which is generally distributed include DMSO, N-methylpyrrolidone, N,N-dimethylacetamide, and formamide, and among them, DMSO is more preferable. When a weak-basic inorganic compound is used as a catalyst as described later, formamide having a high capability of dissolving this catalyst is preferable. The solvents may be used singly, or used in combination of two or more thereof. In addition, 20% by volume or less of solvents other than those described above may be contained as long as required conditions are not lost.

The content of cellulose acetate in the cellulose acetate solution is not particularly limited, but is preferably 1% by mass to 15% by mass, more preferably 3% by mass to 10% by mass from the viewpoint of ensuring that the resulting porous cellulose medium has a practically suitable pore size and a moderate hardness.

Next in the production method of the present invention, the step of mixing a cellulose acetate solution, a deacetylating agent, and a catalyst to obtain a mixed solution is carried out. In the step, the cellulose acetate solution, the deacetylating agent, and the catalyst are mixed, so that deacetylation reaction of the cellulose acetate proceeds to start gelation (liquid-gel phase transition) of the mixed solution.

The deacetylating agent is not particularly limited as long as it can deacetylate cellulose acetate, and a known deacetylating agent can be used. In the present invention, preferred specific examples of the deacetylating agent include alcohols, amines, amino alcohols, and water. Specific examples of the alcohol include aliphatic monohydric alcohols having 1 to 4 carbon atoms such as methanol, ethanol, 1-propanol, 2-propanol, 1-butanol, and 2-methylpropanol; aromatic alcohols such as benzyl alcohol; polyhydric alcohols having 2 to 6 carbon atoms, such as ethylene glycol, 1,3-propylene glycol, 1,2-propylene glycol, glycerin, butane-1,4-diol, butane-1,2,4-triol, pentaerythritol, sorbitol, and xylitol; and monomethyl or monoethyl ethers such as ethylene glycol, diethylene glycol, and triethylene glycol. In addition, examples of the amine include ammonia, aliphatic primary amines having 1 to 5 carbon atoms, aliphatic secondary amines having 1 to 5 carbon atoms, diamines, and benzylamines. Specific examples of the amino alcohol include 2-aminoethanol and 3-aminopropanol. Among them, an alcohol is preferable, and methanol or ethanol is especially preferable when an alkoxide is used as a catalyst as described later. In addition, when an amine compound is used as a catalyst as described later, an amine is preferable. The deacetylating agents may be used singly, or used in combination of two or more thereof.

The use amount of the deacetylating agent is not particularly limited as long as dissolution of cellulose acetate is not impaired, but is preferably about 1.0 to 30 times, more preferably about 1.2 to 15 times the molar amount of acetyl groups of cellulose acetate from the viewpoint of causing deacetylation to occur favorably. In the present invention, a porous cellulose medium with a desired form can be produced by adjusting the use amount of the deacetylating agent together with the use amount of the later-described catalyst to adjust the rate of gelation by deacetylation.

The catalyst is not particularly limited as long as it can catalyze deacetylation reaction of cellulose acetate, but an alkoxide, an amine compound, a weak-basic inorganic compound, a N-hydroxylamine derivative or the like is preferable. Examples of the alkoxide include metal alkoxides of the alcohols exemplified as deacetylating agents. Examples of the metal forming the metal alkoxide include sodium, potassium, lithium, magnesium, calcium, and aluminum. Among these metal alkoxides, sodium alkoxides are preferable, and sodium ethoxide and sodium methoxide are especially preferable. Examples of the amine compound include tertiary amines such as 4-dimethylaminopyridine and 4-pyrrolodinopyridine. Examples of the weak-basic inorganic compound include carbonates, particularly potassium carbonate and cesium carbonate as carbonates having favorable solubility. Examples of the N-hydroxylamine derivative include combinations of a N-oxyimide such as N-oxysuccinimide, N-oxyphthalimide or N-oxybenzotriazole and an amine, or combinations of a N-oxyimide and an equimolar or less amount of an alkali. In addition, examples of the catalyst include salts of compounds having a group: N—OH, such as N-hydroxysuccinimide, N-hydroxyphthalimide, and 1-hydroxybenzotriazole. The catalysts may be used singly, or used in combination of two or more thereof.

Among these catalysts, alkoxides are preferable when an alcohol is used as the deacetylating agent. In addition, when an amine is used as the deacetylating agent, an amine compound is preferable.

In the present invention, the use amount of the catalyst can be freely selected according to the activity of a catalyst to be used, the preferred reaction rate, and the like, and is not particularly limited, but when the use amount of the catalyst is excessively small, the reaction rate (time required for gelation) may be unstable due to inactivation by carbon dioxide in the air or other side reactions (conceivable examples include inactivation caused by formic acid due to hydrolysis of formamide or caused by acetic acid due to hydrolysis of cellulose acetate). From the viewpoint of causing deacetylation to favorably occur, the use amount of the catalyst is preferably about 0.01 mol to 2 mol, more preferably about 0.05 mol to 0.5 mol based on 1 mol of the deacetylating agent. In the present invention, the rate of deacetylation of cellulose acetate by the deacetylating agent can be adjusted by adjusting the amount and type of the catalyst in a mixed solution. Accordingly, for example, when the porous cellulose medium is produced in the form of porous cellulose particles, adjustment of the amount and type of the catalyst enables the mixed solution to turn into a gel at a desired rate in a state in which the mixed solution is dispersed, so that porous cellulose particles formed from a porous cellulose medium are suitably produced as described later. In addition, for example, when the porous cellulose medium is produced in the form of a porous cellulose monolith, adjustment of the amount and type of the catalyst enables the mixed solution to turn into a gel at a rate which allows a porous structure to be formed in the monolith.

The mixed solution may contain other solvents. As the other solvents, for example, the solvent used for preparing the cellulose acetate solution, or the deacetylating agent as a solvent can be used. In addition, for example, the metal alkoxide to be used as the catalyst is generally added to the mixed solution in a state of being dissolved or dispersed in a solvent, and a solvent in which the metal alkoxide is dissolved or dispersed can also serve as the other solvent. The other solvents may be used singly, or used in combination of two or more thereof.

The temperature at which cellulose acetate is subjected to deacetylation reaction in the mixed solution is not particularly limited as long as the mixed solution is not boiled, or frozen and solidified, but the temperature is preferably about −10° C. to 100° C. more preferably about 0° C. to 80° C.

The specific conditions for deacetylation reaction may be appropriately set according to the solubility of each component in the solvent and the reaction rate, and cannot be uniquely determined, but it is preferable to set the conditions so that acetyl groups of cellulose acetate are removed to a degree suitable for a use purpose. For example, the time required for deacetylation, i.e. the time until the mixed solution turns into a gel is, for example, about 1 minute to 48 hours, preferably about 5 minutes to 24 horns. The time required for deacetylation is preferably as short as possible from the viewpoint of suppressing reaggregation of dispersed particles when particles are obtained by dispersion in a dispersion medium. On the other hand, if the gelation rate is excessively high, there may be the problem that uneven gelation occurs before the deacetylating agent or the catalyst is uniformly mixed with the cellulose acetate solution; or gelation occurs before or during dispersion operation performed for preparation of particles, so that spherical particles cannot be obtained. Therefore, the gelation rate may be adjusted so as to give the above-mentioned preferable gelation time. In the present invention, the time required for deacetylation can be reduced by, for example, increasing the amount of the catalyst. However, when the amount of the catalyst is excessively large, it may be impossible to obtain a porous cellulose medium with an appropriate form, and therefore the amount of the catalyst is appropriately adjusted.

In the present invention, after completion of the deacetylation reaction, washing is performed with a solvent which does not adversely affect the resulting porous cellulose (e.g. a solvent exemplified in the separation solvent described later), and a preservative is added if necessary.

In the conventional method, e.g. the method in Patent Document 1, deacetylation is performed after gelation, but in the present invention, gelation of a mixed solution containing cellulose acetate proceeds along with deacetylation of the cellulose acetate. However, a slight amount of unreacted acetyl groups may remain even after the mixed solution turns into a gel, so that the shapes of particles and a monolith are fixed. When the desired function is not accordingly adversely affected, the gel may be used as such for a desired purpose. In addition, when problems caused by remaining of unreacted acetyl groups are to be completely eliminated, the particles or monolith may be treated with a dilute alkali hydroxide (generally sodium hydroxide), ammonia, hydrazine or the like in water or an alcohol. However, for subjecting the resulting particles and monolith to practical separation and purification, crosslinking treatment for improving the strength, or treatment of modification with an active group called a tether for bonding functional groups of proteins and the like is normally performed. Here, in many cases, remaining acetyl groups are unintentionally removed from the gel because the particles or monolith are treated with a strong alkali (normally an aqueous sodium hydroxide solution). Therefore, the gel formed from the mixed solution is not required to be completely deacetylated.

In the production method of the present invention, the porous cellulose medium can be produced in the form of particles (i.e. porous cellulose particles), or in the form of a monolith (i.e. a porous cellulose monolith) according to the shape in gelation of the mixed solution.

For example, when the porous cellulose medium is produced in the form of particles in the production method of the present invention, porous cellulose particles formed from a porous cellulose medium are obtained by mixing the mixed solution with a dispersion medium immiscible with the mixed solution, and allowing deacetylation reaction of the cellulose acetate to proceed in a state in which the mixed solution is dispersed.

The dispersion medium is not particularly limited as long as it is not miscible with the mixed solution, and the mixed solution can be dispersed in the form of particles in the dispersion medium by stirring the dispersion medium together the mixed solution. For example, for preventing the mixed solution from being aggregated in dispersion of the mixed solution, it is preferable that the dispersion medium has a certain degree of viscosity during dispersion of the mixed solution. The viscosity of the dispersion medium is about 0.2 Pa·s to 20 Pa·s at 25° C.

The dispersion medium is preferably nonpolar so as not to be miscible with a solvent or the like contained in the mixed solvent, and specific examples thereof include hydrocarbons having 20 or more carbon atoms, such as liquid paraffin and petrolatum, silicone oil, and fluorinated hydrocarbons. Among them, liquid paraffin is preferable from the viewpoint of cost. The dispersion media may be used singly, or used in combination of two or more thereof.

Petrolatum quickly loses its fluidity at a temperature equal to or lower than a specified softening temperature. Thus, when particles of the dispersed mixed solution are easily reaggregated to form lumps, use of petrolatum is effective for the purpose of increasing the yield of the particles by first preparing a dispersion liquid at a temperature equal to or higher than the softening temperature, and first cooling the dispersion liquid to a temperature equal to or lower than the softening temperature, so that the particles of the mixed solution cannot move and come into contact with one another. The softening temperature of petrolatum varies depending on the type thereof, and can be appropriately selected. However, in the production method of the present invention, adjustment of the amount and type of the catalyst enables the mixed solution to turn into a gel at a desired rate in a state in which the mixed solution is dispersed. Thus, in the production method of the present invention, it is not necessary to suppress reaggregation or the like of the mixed solution using petrolatum or the like when the amount and type of the catalyst are adjusted.

When the porous cellulose medium is formed into particles, it is necessary that the mixed solution containing cellulose acetate be kept in a dispersed state until the mixed solution turns into a gel as deacetylation reaction proceeds after the mixed solution is dispersed in the dispersion medium. Thus, an appropriate dispersion stabilizer may be added to the dispersion medium if necessary.

The dispersion stabilizer is not limited as long as it improves the stability of the dispersion state of the mixed solution, and retards the rate at which particles composed of the mixed solution are aggregated. Examples of the dispersion stabilizer include esters of a polyhydric alcohol such as glycerin, sorbitan, polyglycerin or sucrose with a higher carboxylic acid, and modified silicone containing a small amount of polar groups, and other commercially available dispersion stabilizers can also be used.

As a method for dispersing the mixed solution containing cellulose acetate in the dispersion medium, mention may be made of various methods, which include methods with which a wide particle size distribution is given, and methods with which a monodisperse particle size is given. For example, a method in which a so-called microreader is used, and a mixed solvent formed into a gel is injected from a thinner nozzle into a liquid dispersion medium flowing at an appropriate speed is suitable for preparing particles having a uniform particle size.

In addition, various methods can be used such as a method in which a mixed solution is extruded into a dispersion medium from a film having a certain pore size; a method in which a flowable mixed solution is added in an inner cylinder having a hole with a certain size, the cylinder is rotated in a dispersion medium, and the mixed solution formed into a gel is extruded by a centrifugal force; a method in which a dispersion medium containing a dispersion stabilizer if necessary and a flowable mixed solution are fed into a column packed with beads having a certain size;

a method in which a flowable mixed solution is injected into a dispersion medium through a vibration nozzle; and a method using (ultra)sonic waves.

In examples as described later, a method for dispersion by stirring is shown as an example. This method is a method in which the mixed solution is added to the dispersion medium, a strong shear force is applied to generate roughly spherical particles composed of the mixed solution, and the mixed solution in the form of dispersed droplets is deacetylated to turn into a gel. Conditions for stirring and mixing may be appropriately selected according to the target average particle size. The method for dispersion by stirring gives a mixture with various particle sizes, but is the simplest method which does not require a special apparatus.

Preferably, the mixed solution dispersed in the dispersion medium is left standing for about 1 minute to 48 hours, preferably about 5 minutes to 24 hours, so that deacetylation reaction proceeds in the particles composed of the mixed solution.

When the porous cellulose medium is in the form of particles, the step of mixing a separation solvent for separation of porous cellulose particles dispersed in the dispersion medium with a dispersion medium in which porous cellulose particles are formed, so that the porous cellulose particles are separated in the separation solvent may be further carried out.

The separation solvent is preferably one that is not miscible with the dispersion medium, and does not dissolve cellulose, but are miscible with other components (the above-mentioned solvent, catalyst, and deacetylating agent, reaction products other than cellulose, and so on) among components contained in the gel of the mixed solution. Accordingly, among components contained in the gel of the mixed solution, generated cellulose particles can be separated from components of the dispersion medium etc. while the cellulose particles are prevented from being dissolved again and deformed by an external force.

Examples of the separation solvent may include water, methanol, ethanol, 2-propanol, acetamide, formamide, and mixtures thereof. Among them, water is preferably used from the viewpoint of ease of handling.

Porous cellulose particles in a state of being dispersed in the dispersion medium can be directly separated by filtration, but since the dispersion medium generally has a high viscosity, the risk of deforming or collapsing porous cellulose particles by application of a pressure in filtration increases. It is also possible to reduce the pressure during filtration by adding to the dispersion medium a low-viscosity liquid miscible with the dispersion medium.

The resulting porous cellulose particles are washed by an appropriate method using water or an alcohol such as methanol or ethanol, and stored in a state of moisture. When the particles are dried, an appropriate amount of a saccharide, glycerin or the like is added. When the particles are stored in moisture for a long period of time, a preservative such as an alcohol or sodium azide is added to prevent rotting. The particles can also be dried with glycerin, saccharides, urea or the like added thereto. When used, the particles are packed in a column by a conventional method.

Among the porous cellulose particles (particulate porous cellulose medium) obtained by the production method of the present invention, substantially spherical or spherical particles having a particle size (maximum diameter) of about 10 μm to 300 μm can be selected, and used as a filler for chromatography. As chromatography, mention may be made of size exclusion chromatography.

Availability of the particles in size exclusion chromatography means that the particles can be used in chromatographic separations in various modes other than size exclusion by bonding an appropriate ligand. These modes include modes of ion exchange, hydrophobicity, and affinity.

Generally, for separating and purifying macromolecules to be produced in biotechnology, such as hormones, enzymes, and antibody medicines, a matrix having pores with a size enabling these substances to sufficiently enter. That is, when using a column packed with porous cellulose particles, gel filtration chromatography is performed with water as a mobile phase, it is desirable that fractionation occur in some molecular weight region in a range of approximately $10^3$ to $10^7$ in terms of a molecular weight of polyethylene glycol.

The size of the pores of the porous cellulose medium can be adjusted depending on the concentration of cellulose acetate, the amount and type of a solvent in which the cellulose acetate is dissolved, a catalyst, and a deacetylating agent, and the conditions (particularly temperature) for gelation of the mixed solution.

On the other hand, when the porous cellulose medium is produced in the form of a monolith in the production method of the present invention, a porous cellulose monolith formed from a porous cellulose medium is obtained by allowing deacetylation reaction of cellulose acetate to proceed in a state in which the mixed solution is left standing with an arbitrary shape.

The monolith is an integrated lump of a porous material. In the chromatography using a particulate filler, a developing solution also passes through fine pores of the particles, but most of the developing solution passes through interparticle gaps. On the other hand, in the monolith, the developing solution passes through micropores of the integral porous material. Thus, it is preferable to reduce resistance to the flow of the developing solution, conditions for giving a structure suitable for this purpose are selected, and the solid content is set lower than that in the case of a particulate filler in general. However, except for the case of using the monolith as a filtration material, the essential mechanism of separation is the same as in the case of the particulate filler.

In liquid chromatography, it is extremely important that the developing solution moves at the same speed in any part of the separating agent to form a so-called piston flow. In the filler, variations in characteristics of individual particles are reduced by mixing, and therefore a slight difference in properties between the particles is acceptable, but uniformity of the interparticle gaps bearing a part of the liquid with a high flow is important. For this, a technique in packing of the filler in a container called a column is important.

On the other hand, in monoliths, it is extremely important that the generated porous structure is uniform in a direction perpendicular to the flow of the developing solution and that gaps through which a liquid easily flows are not generated between the monolith and the container. The uniform porous material in the perpendicular direction described here cannot be prepared by contact with a gelling agent (precipitant), or evaporation of a solvent as a known technique.

The production method of the present invention is suitable for production of a porous cellulose monolith because adjustment of the amount and type of the catalyst enables the mixed solution to turn into a gel at a rate which allows a porous structure to be formed in the monolith.

In preparation of the porous cellulose monolith, the mixed solution is added in a molding container with an arbitrary shape, and then left standing for about 1 minute to 48 hours, preferably about 4 minutes to 24 hours, so that deacetylation reaction of cellulose acetate takes place. Accordingly, when gel of the mixed solution is formed, and the resulting gel is washed with an appropriate solvent directly or after being taken from the container, the monolith can be used as a separating agent or the like. In general, it is preferable to avoid drying because drying may cause deformation of the shape of the monolith, or eliminate fine pore structures, but it is possible to perform drying when an appropriate nonvolatile additive coexists. As the nonvolatile additive, glycerin, sucrose, trehalose, sugars such as thick malt syrup and sugar alcohols, various amides, DMSO, and the like are suitable.

For evaluating the properties of the porous cellulose monolith, it is necessary to put the porous cellulose monolith in an appropriate container in such a manner that a gap is not generated, and localized consolidation does not occur. The method for this may be any known method. Normally, when a porous cellulose monolith is formed by gelation, slight shrinkage often occurs, so that a gap is generated between the porous cellulose monolith and the container. In this case, the porous cellulose monolith can be put in the container without generating a gap by modifying the wall surface of the container with a chemical structure having a strong affinity with a cellulose-based substance (e.g. bonding cellulose to the surface), or utilizing shrinkage/swelling caused by a change of the environment of gel, or making the container size adoptable.

In the present invention, an adsorbent can be produced by immobilizing an affinity ligand on the porous cellulose medium obtained by the above-described production method. That is, when the method for producing a porous cellulose medium according to the present invention further includes the step of immobilizing the affinity ligand, an adsorbent to which the affinity ligand is bonded can be produced. This adsorbent can also be used as a separating agent for affinity chromatography. The porous cellulose medium according to the present invention can be used as a separating agent or an adsorbent for affinity chromatography by binding an affinity ligand irrespective of whether the porous cellulose medium is in the form of a porous cellulose monolith or porous cellulose particles.

Hereinafter, in the present invention, a method for producing an adsorbent to be used in an affinity mode will be described in detail. A protein can be used as the affinity ligand. Examples of the protein that can be used in the present invention include substances having a molecular weight of 3 to 300 kDa, preferably 30 to 150 kDa, and having affinity with a protein to be separated, such as an antibody. Among them, protein A, protein G, protein L, and functional variants thereof are preferable because they have high selectivity when used for separation of a protein of an antibody.

When separation of an antibody is a main purpose, the ligand is preferably one that can be specifically bonded to a part of immunoglobulin. The functional variant is a protein having at least one modification in the natural amino acid sequence, and still retaining at least one function associated with the natural sequence. Natural sequences include naturally occurring amino acid sequences. The change of the amino acid may lie substitution of one or more amino acids for another amino acid, deletion of one or more amino acids and or addition of one or more amino acids, or any combination of thereof. Mention is also made of a mode such as a combination of addition, deletion, and substitution applied to a natural sequence. The functional variant may also include a fragment or a domain of a protein. The amino acid sequence of the functional valiant may be identical to the natural amino acid sequence by at least 70%, by at least 75%, by at least 80%, by at least 85%, by at least 90%, by at least 95%, or by at least 98%, and still retains at least one function associated with the natural sequence.

The loading amount of the protein on the porous cellulose medium is preferably about 1.0 part by mass to 25 parts by mass based on 100 parts by mass of the porous cellulose medium. In addition, the loading amount is preferably about 1 mg to 50 mg per 1 ml of the volume of the porous cellulose medium.

Examples of the specific method for immobilizing an affinity ligand on the porous cellulose medium include a method using a crosslinking agent. The crosslinking agent is not particularly limited, and examples thereof include halohydrin such as epichlorohydrin, epibromohydrin, and dichlorohydrin, bisoxirane, and polyoxirane.

When a crosslinking agent is used, the porous cellulose medium may be crosslinked, followed by activating the crosslinked porous cellulose medium before the porous cellulose medium is reacted with the affinity ligand. For example, by introducing a known reactive functional group, the crosslinked porous cellulose medium can be activated. For example, by activating the porous cellulose medium with cyanogen bromide (CNBr), N,N'-disuccinimidyl carbonate ester (DSC), epoxide, activated carboxylic acid (NHS ester) or the like, the functional group can be changed into a functional group with which a compound to be immobilized as a ligand reacts more easily than a functional group originally possessed by the porous cellulose medium. Thereafter, the adsorbent can be produced by passing through the step of reacting the porous cellulose medium with a compound to be immobilized as a ligand, thereby immobilizing the ligand and the porous cellulose medium.

In addition, examples of the method for producing other adsorbent include a method in which a condensation reagent such as carbodiimide, or a reagent having a plurality of functional groups in the molecule, such as glutaraldehyde, is added to a system in which a porous cellulose medium and a compound to be immobilized as a ligand are present, so that condensation and crosslinking are performed to immobilize the porous cellulose medium and the ligand, thereby obtaining an adsorbent.

As another mode of bonding the porous cellulose medium and the affinity ligand, mention may be made of a mode in which a formyl group is introduced into the porous cellulose medium to react the formyl group with an amino group of the protein. For the reaction for introducing a formyl group, mention may be made of, for example, a method in which a polysaccharide having a hydroxyl group of vicinal is oxidized by a periodate oxidation method to form a formyl group on a sugar-chain.

In addition, mention is made of a method in which through various spacers obtained by a method including reacting a periodate, etc., a formyl group is introduced to a glyceryl group obtained by ring opening of an epoxy group. For example, an amino sugar such as glucosamine can be used as a spacer.

Examples of the method for bonding a formyl group of the porous cellulose medium to a protein such as protein A include known methods, and mention may be made of, for example, a mode in which a porous cellulose medium into which an amino sugar such as glucosamine is introduced as a spacer is reacted with a solution containing protein A. Examples of the method include a method as described in Japanese Patent Laid-open Publication No. 2008-279366.

Various target molecules can be purified by using the adsorbent obtained by bonding the affinity ligand to the porous cellulose medium prepared by the production method of the present invention as described above.

Examples of the target molecule may include proteins such as immunoglobulins. Examples of the immunoglobulin may include polyclonal antibodies, monoclonal antibodies, and functional fragments thereof.

The purification method according to the present invention includes the following steps. The method includes a first step of bonding the target substance to an affinity ligand by bringing an adsorbent, which is obtained by bonding the affinity ligand to the porous cellulose medium produced by the production method of the present invention, into contact with a mixture containing the target substance; and a second step of separating the target substance bonded to the affinity ligand of the adsorbent.

The method for separating a target substance bonded to the affinity ligand of the adsorbent includes changing the pH or changing the salt concentration between the first step and the second step. Specifically, for example, the pH in the first step is set to a neutral pH such as a pH of 6 to 8, and the pH in the second step is set to an acidic pH such as a pH of less than 6. For example, the salt concentration is set to less than 0.1 M in the first step, and set to 0.1 M or more in the second step, or set to the 0.1 M or more in the first step, and set to less than 0.1 M in the second step. While the porous cellulose medium has been described above with purification of an immunoglobulin as an example, the porous cellulose medium can be used for various purposes in addition to the above-mentioned purpose, such as purification of enzymes, plasma proteins, vaccines, and the like, and adsorption and removal of lipopolysaccharides with an ion-exchange group, cyclodextrin, dye (e.g. CIBA Chron-blue) or the like bonded as a ligand.

EXAMPLES

Hereinafter, the present invention will be described in detail below by showing examples and comparative examples. It is to be noted that the present invention is not limited to examples.

Example 1: Preparation of Porous Cellulose Monolith 0.40 g of cellulose diacetate (acetylation degree: 55% and substitution degree; 2.5) was dissolved in 4.65 g of DMSO. When 1.00 mL of methanol was added to the solution, a precipitate was formed once, but when the solution was thoroughly stirred, it turned to a homogeneous solution (cellulose diacetate solution) again, and the solution was left standing while being cooled with ice. Meanwhile, 0.50 mL of each of DMSO and methanol was mixed, 1.04 mg of a 20% sodium ethoxide/ethanol solution (manufactured by Wako Pure Chemical industries, Ltd.) was mixed therewith, and the mixture was cooled with ice. Next, this solution and the cellulose diacetate solution were quickly mixed, and the mixture was poured into a columnar cell of 1 cm square, and subsequently cooled with ice. The liquid in the columnar cell was solidified in about 2 hours. The resulting solid was further cooled with ice for 2 hours, and then placed overnight at room temperature, and a quadrangular prismatic porous cellulose monolith was then taken out from the columnar cell, and repeatedly washed with water. The obtained porous cellulose monolith had a columnar shape of 7.0 mm square.

Next, a part of the obtained porous cellulose monolith was cut off to obtain a small piece (about 5 mm×3 mm×2 mm). Next, the obtained small piece was dried, an infrared absorption spectrum was then measured by a KBr method, and resultantly, the porous cellulose monolith was supposed to be substantially composed of cellulose although a trace of C=O stretching vibration was shown at 1740 cm$^{-1}$. Next, water deposited on the surface of this small piece was sucked, and weighed. Further, the small piece was held at 80° C. until having a constant weight, and then weighed to measure the cellulose component ratio in the porous cellulose monolith, and the result showed that the cellulose component ratio was 11.0% by mass. The small piece was immersed in methanol, and the section was then put in liquid nitrogen, and resultantly broken naturally in liquid nitrogen. Next, the fragments in liquid nitrogen were dried with supercritical carbon dioxide, and resultantly a thin hazy solid remained. The specific gravity of the solid was about 0.25 as determined from the weight and the external form. Since the specific gravity of cellulose is generally about 1.5, the solid is obviously aerogel. FIG. 1 shows an image of an electron micrograph of the broken surface (naturally broken in liquid nitrogen). As is apparent from the image in FIG. 1, a net-like porous structure was observed on the broken surface.

Figure 2:
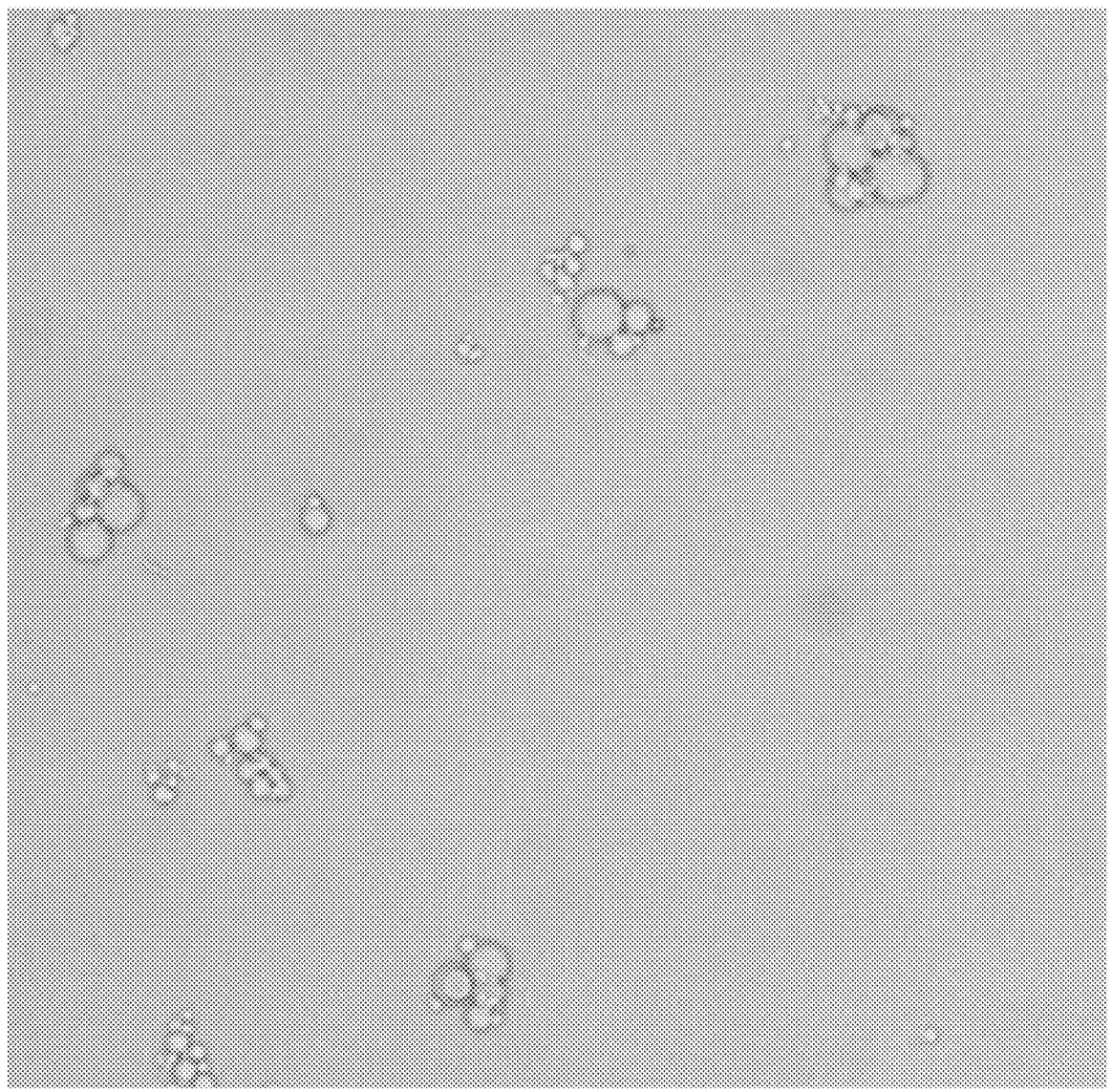
FIG. 2 is an optical micrograph of gel beads obtained in Example 2.

Example 2: Preparation of Porous Cellulose Particles 10 mL of methanol was added to 51.6 g of a DMSO solution (cellulose diacetate: 7.88% by mass) of cellulose diacetate (acetic acid content: 55%), the mixture was thoroughly stirred to obtain a homogeneous transparent solution, and the solution was cooled with ice (solution 1). On the other hand, a mixed solution (about 50 ml) of DMSO/methanol (46.5:15 (v/v)) was brought into contact with about 1000 mL of liquid paraffin for 1 day, and then the mixed solution was separated and removed to obtain 800 ml of liquid paraffin saturated with DMSO/methanol (manufactured by Kanto Chemical Co., Inc., specific gravity: 0.89 to 0.91). The liquid paraffin was put in a 1 L container, and cooled with ice (solution 2). In addition, 5.0 mL of DMSO, 5.0 mL of methanol, and 187 mg of a 20% sodium ethoxide/ethanol solution (manufactured by Wako Pure Chemical Industries, Ltd.) were mixed, and the mixture was cooled with ice (solution 3). Next, solution 1 and solution 3 were mixed, and thoroughly stirred, the mixture was then put in solution 2, and the mixture was stirred using a stirring blade with a diameter of 2 cm at 740 rpm for 5 minutes. After the mixture was stirred, the mixture was left standing and cooled for 4 hours with ice, and then allowed to stand overnight at room temperature. Next, about 200 mL of water was added, the mixture was then gently stirred, and the lower layer (aqueous phase) was sucked up into another container. The operation of adding water and sucking up the lower layer was repeated three times in total to extract a cellulose component. Next, the obtained aqueous phase was left standing, the supernatant was decanted, and concentrated to about 200 mL, 1 g of NaOH was then added, and the mixture was further left standing overnight to obtain porous cellulose particles. FIG. 2 shows an optical micrograph of the obtained gel particles. From the optical micrograph, it was confirmed that the porous cellulose particles mainly included spherical particles with a diameter of about 50 μm or less.

Example 3: Preparation of Porous Cellulose Monolith 16.03 g of cellulose diacetate was dissolved in 129.42 g of DMSO to prepare a solution. 7.6 mL of methanol was gently mixed with 3.04 g of the solution to obtain a transparent solution, and the solution was cooled with ice. On the other hand, a solution was prepared by diluting 0.117 g of a 10% methanol solution of lithium methoxide (manufactured by Wako Pare Chemical Industries, Ltd.) with 1.94 g of methanol and 2.77 g of DMSO, and cooled with ice. 1.00 mL of the diluted solution of lithium methoxide was mixed with the cellulose diacetate solution, and the mixture was quickly mixed, and then dispensed into two 1 cm prismatic cells. The liquid in one of the ceils lost fluidity after about 3 hours when cooled with ice, and the liquid in the other cell lost fluidity after 30 minutes when immersed in water at about 20° C. In each case, a white translucent gel-like solid was obtained.

Example 4: Preparation of Porous Cellulose Monolith 7.22 g of cellulose diacetate (acetic acid content: 55%) was dispersed in 112.21 g of formamide, the dispersion was heated to 125° C. for about 30 minutes with stirring to obtain a clear solution, and the solution was cooled to room temperature. On the next day, 8.68 g of the soft gel-like solution was collected, and mixed with 1.58 g of methanol, so that a flowable solution was ultimately obtained. On the other hand, 120 mg of potassium carbonate was dissolved in 2 mL of formamide, and both the solutions were cooled with ice. 1.00 mL of a potassium carbonate solution was added to the solution to which methanol had been added, and the mixture was kept at 0° C. for 3 minutes while being thoroughly stirring, and was poured in two quadrangular prismatic plastic cells which were 100 cm on each side. The liquid in one of the cells lost fluidity after 2 hours when kept at 0° C. The liquid in the other cell lost fluidity after 23 minutes when left standing at room temperature, i.e. 23° C. The liquid was allowed to stand overnight, a gel-like solid slightly shrunk and separated from the container was then thoroughly washed in pure water for 2 days while the water was replaced. Each of the obtained gels was an opaque white solid. A part of the gel was cut off, water deposited on the surface was soaked up with a filter paper, the gel was then weighed, and dried at 80° C. and normal pressure for 3 hours, then at 80° C. under reduced pressure (about 1 Torr) for 3 hours, and the gel shrunk to diminish in size and turned transparent was weighed to examine the water content of the original gel. The gel having a weight of 163.2 mg when formed at 0° C. had a weight of 11.8 g after being dried, and therefore the water content of the gel was 92.8%. In addition, the gel having a weight of 133.5 mg when formed at 23° C. had a weight of 9.5 g after being dried, and therefore the water content of the gel was 92.9%.

Example 5

Figure 3:
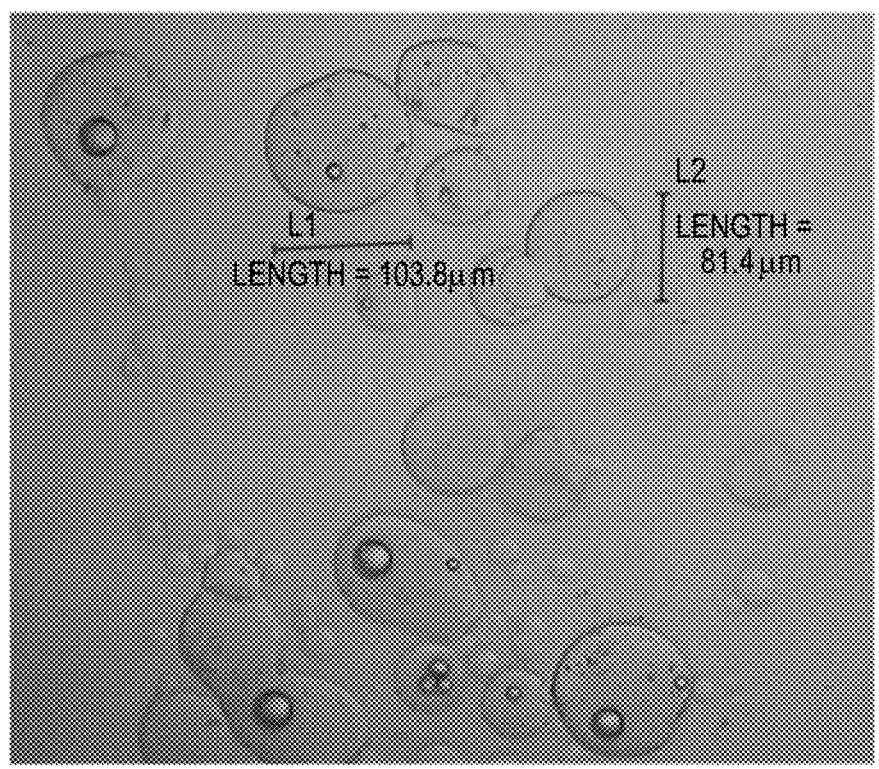
FIG. 3 is an optical micrograph of beads obtained in Example 5.
Figure 4:
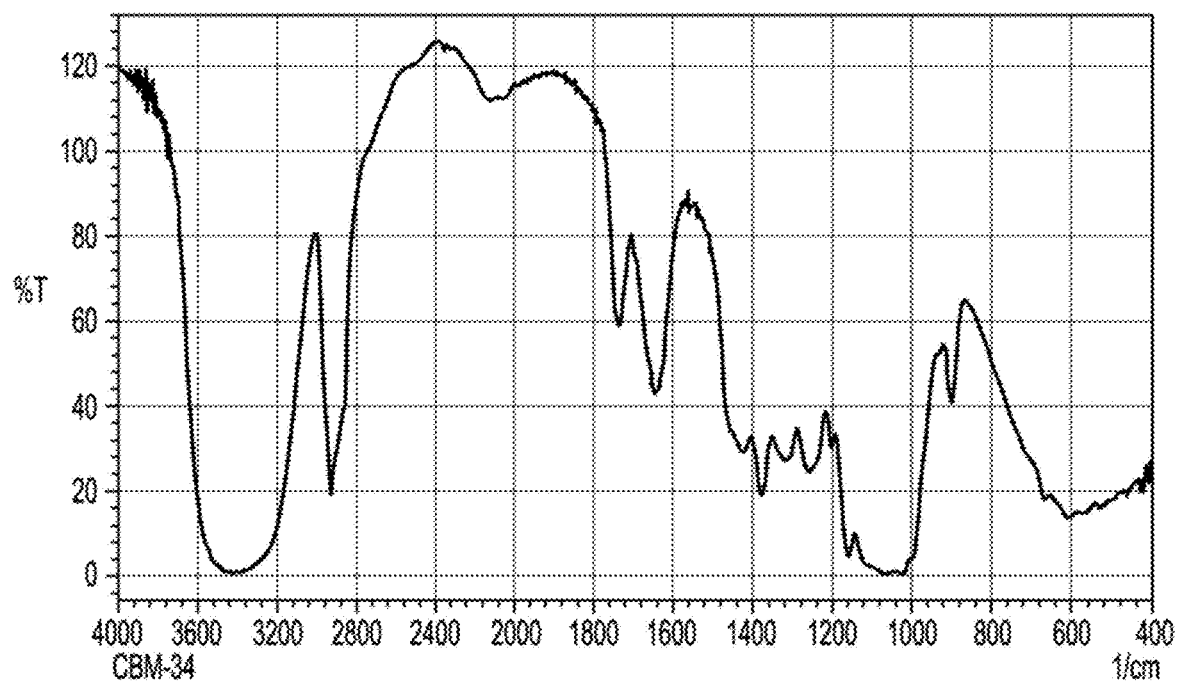
FIG. 4 is an infrared absorption spectrum measured in Example 5.

As in Example 2, 384 mg of TSG-10 manufactured by Nihon Emulsion Co., Ltd. was added to 790 mL of liquid paraffin saturated with a mixed liquid of formaldehyde and methanol (1:4 v/v) by bringing the liquid paraffin in contact with the mixed liquid, and the mixture was heated to 60° C. to dissolve the liquid paraffin, and kept at 20° C. (solution 5). On the other hand, a flowable solution was obtained by mixing 19.3 g of methanol with 109.2 g of a formamide solution of cellulose diacetate formamide used in Example 4, and the flowable solution was kept at 20° C. (solution 4). A solution (solution 6) of 620 mg of potassium carbonate in 12.9 g of formamide was poured in solution 4, and the mixture was mixed. After the mixing, the mixed liquid was quickly poured in solution 5, and the mixture was stirred at about 400 rpm for 8 minutes using a stirring blade. The mixture was left standing overnight, 150 mL of water was then added, the container was rotated, the thus obtained while powdered beads were extracted with water, and the liquid was separated. The same operation was further repeated twice, and the water extract liquids were combined. Sedimentation in water and decantation of the supernatant were repeated to obtain beads with a sedimentation volume of 70 mL. FIG. 3 shows an optical micrograph of the beads. FIG. 4 shows an infrared absorption spectrum measured by a KBr disk method for the obtained particles sequentially washed with methanol and 2-propanol, then dried, in the infrared absorption spectrum, an absorption thought to be given by a carbonyl group of an acetyl group is shown in the vicinity of $1735\ cm^{-1}$, but the absorption is weaker than the essentially weak absorption in the vicinity of $2920\ cm^{-1}$, and thus the product can be considered to be cellulose.

The invention claimed is:

1. A method for producing a porous cellulose medium, the method comprising the steps of:
   preparing a cellulose acetate solution with cellulose acetate dissolved in a solvent;
   mixing the cellulose acetate solution, a deacetylating agent, and a catalyst to obtain a mixed solution; and
   stirring the mixed solution to maintain the components in dissolved form until deacetylation of the cellulose acetate proceeds;
   wherein, in the mixed solution, deacetylation of the cellulose acetate proceeds, leading to occurrence of a liquid-gel phase transition.

2. The method for producing a porous cellulose medium according to claim 1, wherein the catalyst is at least one selected from the group consisting of an alkoxide, an amine compound, a weak-basic inorganic compound, and a N-hydroxyamine derivative.

3. The method for producing a porous cellulose medium according to claim 2, wherein the amine compound is a tertiary amine, and the weak-basic inorganic compound is a carbonate.

4. The method for producing a porous cellulose medium according to any one of claims 1 to 3, wherein a porous cellulose monolith formed from the porous cellulose medium is obtained by allowing a deacetylation reaction of the cellulose acetate to proceed in a state in which the mixed solution is left standing in a molding container.

5. The method for producing a porous cellulose medium according to claim 1, wherein porous cellulose particles formed from the porous cellulose medium are obtained by mixing the mixed solution with a dispersion medium immiscible with the mixed solution, and allowing a deacetylation reaction of the cellulose acetate to proceed in a state in which the mixed solution is dispersed.

6. The method for producing a porous cellulose medium according to claim 5, wherein the dispersion medium is liquid paraffin.

7. The method for producing a porous cellulose medium according to claim 1, wherein the catalyst comprises at least one of an alkoxide and a N-hydroxyamine derivative.

8. The method for producing a porous cellulose medium according to claim 1, wherein the deacetylating agent comprises at least one of an alcohol, an amine, an amino alcohol, and water.

9. The method for producing a porous cellulose medium according to claim 1, wherein the deacetylating agent comprises an amine.

10. The method for producing a porous cellulose medium according to claim 1, wherein the deacetylating agent comprises at least one of aliphatic monohydric alcohols having 1 to 4 carbon atoms, aromatic alcohols, polyhydric alcohols having 2 to 6 carbon atoms, monomethyl ethers, and monoethyl ethers.

11. The method for producing a porous cellulose medium according to claim 1, wherein the deacetylating agent comprises at least one of ammonia, aliphatic primary amines having 1 to 5 carbon atoms, aliphatic secondary amines having 1 to 5 carbon atoms, diamines, and benzylamines.

12. The method for producing a porous cellulose medium according to claim 1, wherein the deacetylating agent comprises at least one of 2-aminoethanol and 3-aminopropanol.

13. The method for producing a porous cellulose medium according to claim 1, wherein the deacetylating agent is methanol and the catalyst is potassium carbonate.

* * * * *